United States Patent [19]

Revane

[11] Patent Number: 5,064,414
[45] Date of Patent: Nov. 12, 1991

[54] LOCKING CLIP WITH SHEATH AND DILATOR

[75] Inventor: James E. Revane, Excelsior, Minn.

[73] Assignee: Angeion Corporation, Plymouth, Minn.

[21] Appl. No.: 642,930

[22] Filed: Jan. 18, 1991

Related U.S. Application Data

[63] Continuation of Ser. No. 386,204, Jul. 28, 1989, abandoned.

[51] Int. Cl.$^5$ .................................. A61M 25/06
[52] U.S. Cl. ............................. 604/165; 604/264; 24/543
[58] Field of Search ............... 604/158, 161, 164, 165, 604/263, 280; 24/333, 543

[56] References Cited

U.S. PATENT DOCUMENTS

| | | | |
|---|---|---|---|
| 772,114 | 10/1904 | Pappenheim | 604/220 |
| 2,630,803 | 3/1953 | Baran | 604/158 |
| 2,705,949 | 4/1955 | Silverman | 604/165 X |
| 2,875,761 | 3/1959 | Helmer et al. | 604/210 |
| 4,191,186 | 3/1980 | Keeler | 604/164 |
| 4,231,367 | 11/1980 | Rash | 604/165 |
| 4,233,974 | 11/1980 | DeSecki et al. | 604/165 |
| 4,256,119 | 3/1981 | Gauthier | 604/165 X |
| 4,596,559 | 6/1986 | Fleischhacker | 604/170 |
| 4,772,266 | 9/1988 | Grashong | 604/164 |
| 4,966,588 | 10/1990 | Rayman et al. | 604/165 |

Primary Examiner—John D. Yasko
Assistant Examiner—Adam J. Cermak
Attorney, Agent, or Firm—Hugh D. Jaeger

[57] ABSTRACT

A locking clip for placement between a dilator and a sheath for releasably securing a dilator and a sheath together during an insertion procedure. The locking clip includes a back support, a snap ring for engaging about a hub of the dilator at one end of the back support and at least one tooth at a lower end of the back support for engaging under a tab of the sheath. The sheath can be a tear-away sheath.

1 Claim, 5 Drawing Sheets

LOCKING CLIP WITH SHEATH AND DILATOR

This application is a continuation of application Ser. No. 07/386,204, filed July 28, 1989, now abandoned.

BACKGROUND OF THE INVENTION

1. Field of the Invention

The present invention pertains to a locking clip for use with a dilator and a sheath. The locking clip releasably secures the dilator and the sheath together during an insertion procedure into a vein of a person. The sheath can be a tear-away sheath.

2. Description of the Prior Art

During insertion of a sheath with a dilator into a person, it some times happens that the dilator slides out of the sheath, complicating this type of a medical insertion procedure. This causes problems in that the insertion procedure of the sheath and the dilator is ineffective, the sheath may not smoothly slide into the vein, the sheath may even go through the vein or attempt to break or bend, or separate along a score line or a tear-away line of the sheath. Blood may also back flow through the sheath in the event the dilator "pops out", and possibly the blood may even gushingly back flow through the sheath.

Prior art surgical procedures have required that the surgeon maintain a secure grip between the dilator and the sheath, which is not always possible, and further not always practical depending upon the surgeon's dexterity.

The present invention overcomes the disadvantages of the prior art by providing a locking clip for engaging between the hub of the dilator and at least one of the tabs of the sheath.

SUMMARY OF THE INVENTION

The general purpose of the present invention is to provide a locking clip which locks the dilator hub of a dilator to at least one of the tabs of a sheath, providing an integral unit of a locking clip-dilator-sheath during an insertion procedure.

According to one embodiment of the present invention, there is provided a locking clip including a back support, a snap ring at one end of the back support, and a clip at the other end of the back support. The snap ring engages about the hub of the dilator, and the clip engages about one of the tabs of the sheath. Together, the locking ring between the hub of the dilator and the tab of the sheath provides an integral locking clip-dilator-sheath unit. The sheath can be a tear-away sheath. The sheath can also be an introducer in lieu of a sheath.

Significant aspects and features of the present invention include a locking ring which provides an integral unit of a locking clip-dilator-sheath unit which also provides for ease of insertion during a surgical procedure. This overcomes the problems of the prior art where the dilator would tend to slide out of the sheath.

Another significant aspect and feature of the present invention is to provide releasable securement of the locking clip for the dilator and the sheath so that the dilator and sheath has the structural support of the locking clip as required during an insertion procedure.

A further significant aspect and feature of the present invention is a locking clip which can be used with a sheath, tear-away sheath or an introducer.

Having thus described the embodiments of the present invention, it is a principal object hereof to provide a locking clip for engagement between a dilator and a sheath, tear-away sheath or an introducer. For purposes of disclosure and illustration, the terms sheath, tear-away sheath or introducer are applicable to the teachings of the locking clip releasably engaging a first member, such as a dilator, and a second member, such as the sheath, tear-away sheath or introducer.

One object of the present invention is for the locking clip to provide an integral unit between the locking clip, the dilator and the sheath.

Another object of the present invention is to provide a dilator which is integral to a sheath through the locking clip, providing an integral unit for use during an insertion procedure.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
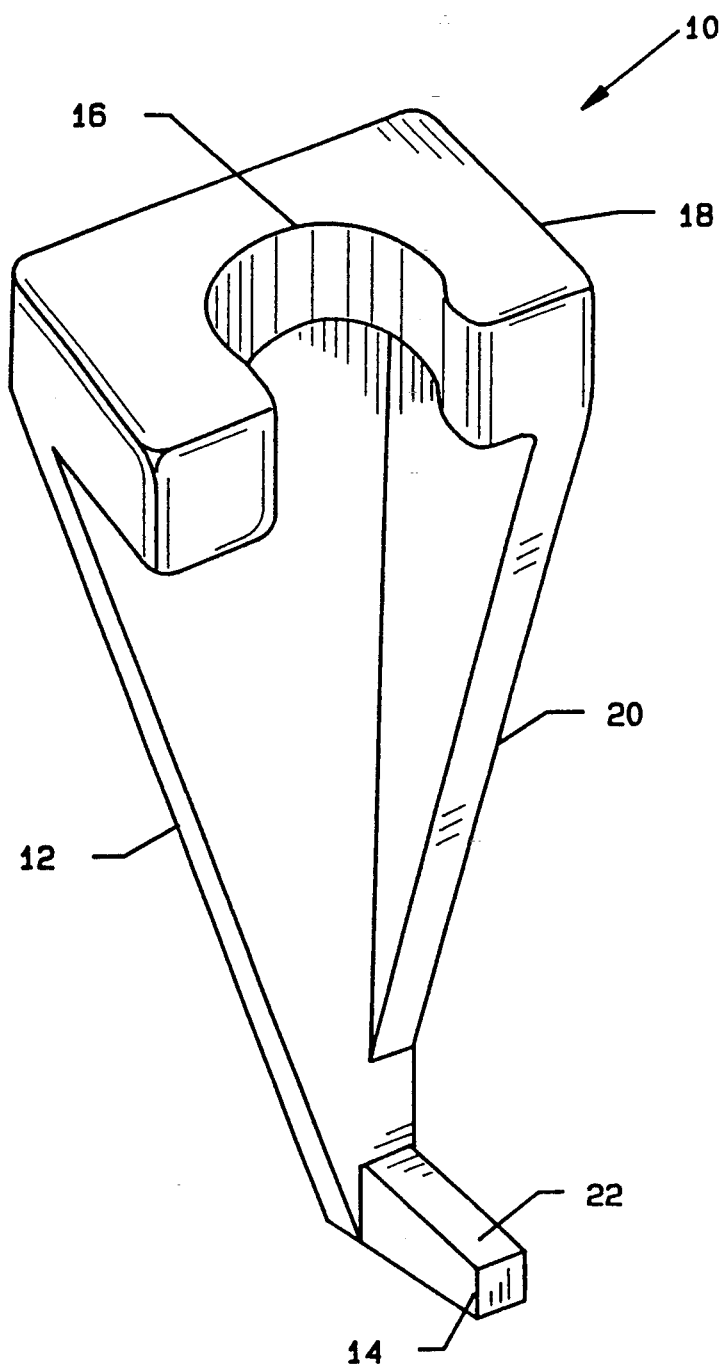
FIG. 1 illustrates a perspective view of the locking clip.

FIG. 1 illustrates a perspective view of a locking clip 10 including a back support 12 of an angular geometrical configuration, a locking tooth 14 with a tooth surface 22 secured to one end of the back support 12, a snap ring 16 in a snap ring support member 18 secured to the other end of the back support 12, and an optional side support 20 extending between a lower portion of the back support 12 and the snap ring support member 18. The locking clip 10 can be of a suitable polymer material such as polyethylene or polypropylene. The locking clip 10 can be injection molded of the suitable polymer material forming a one piece integral member. The placement of the locking tooth 14 and side support 20 is dependent upon the geometrical characteristics of the dilator and the sheath.

Figure 2:
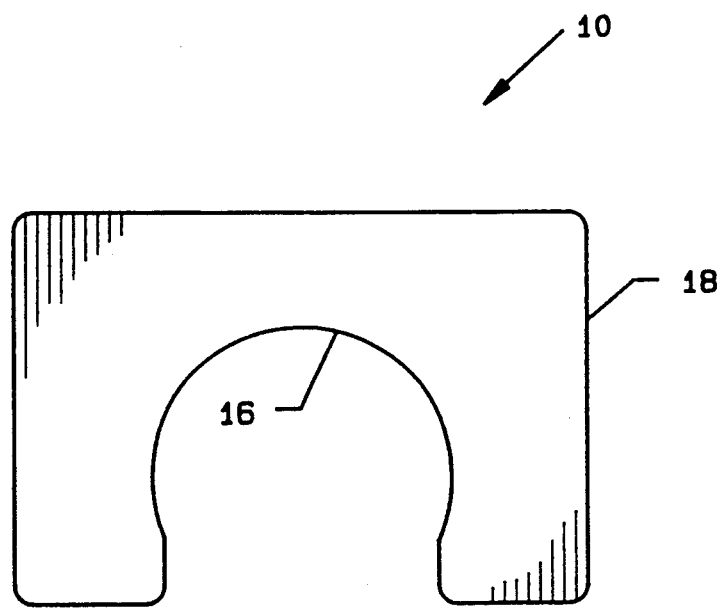
FIG. 2 illustrates a top view of the locking clip.

FIG. 2 illustrates a top view of the locking clip 10 where all numerals correspond to those elements previously described.

Figure 3:
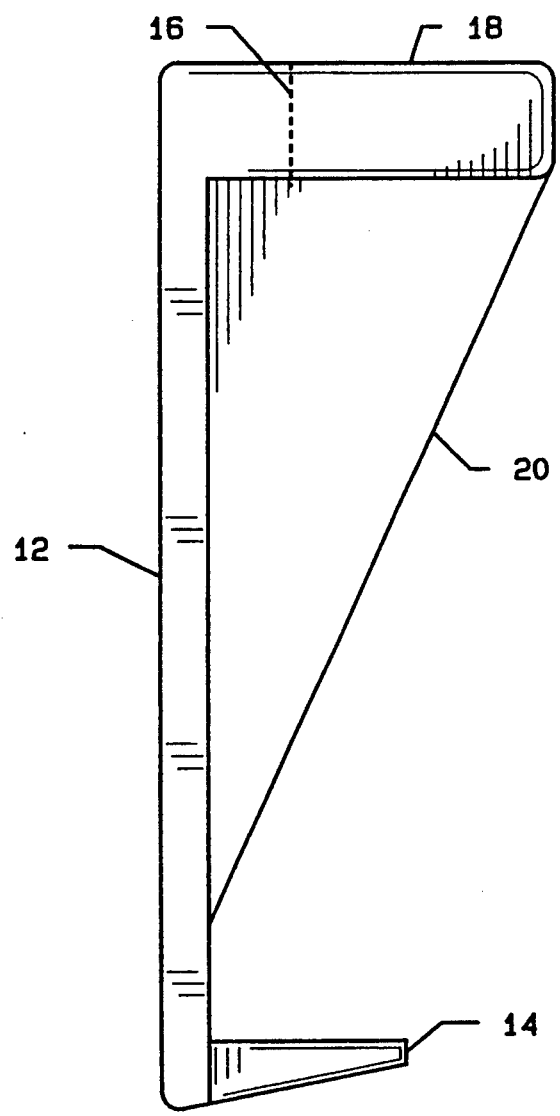
FIG. 3 illustrates a left side view of the locking clip.

FIG. 3 illustrates a left side view of the locking clip 10 where all numerals correspond to those elements previously described.

MODE OF OPERATION

Figure 4:
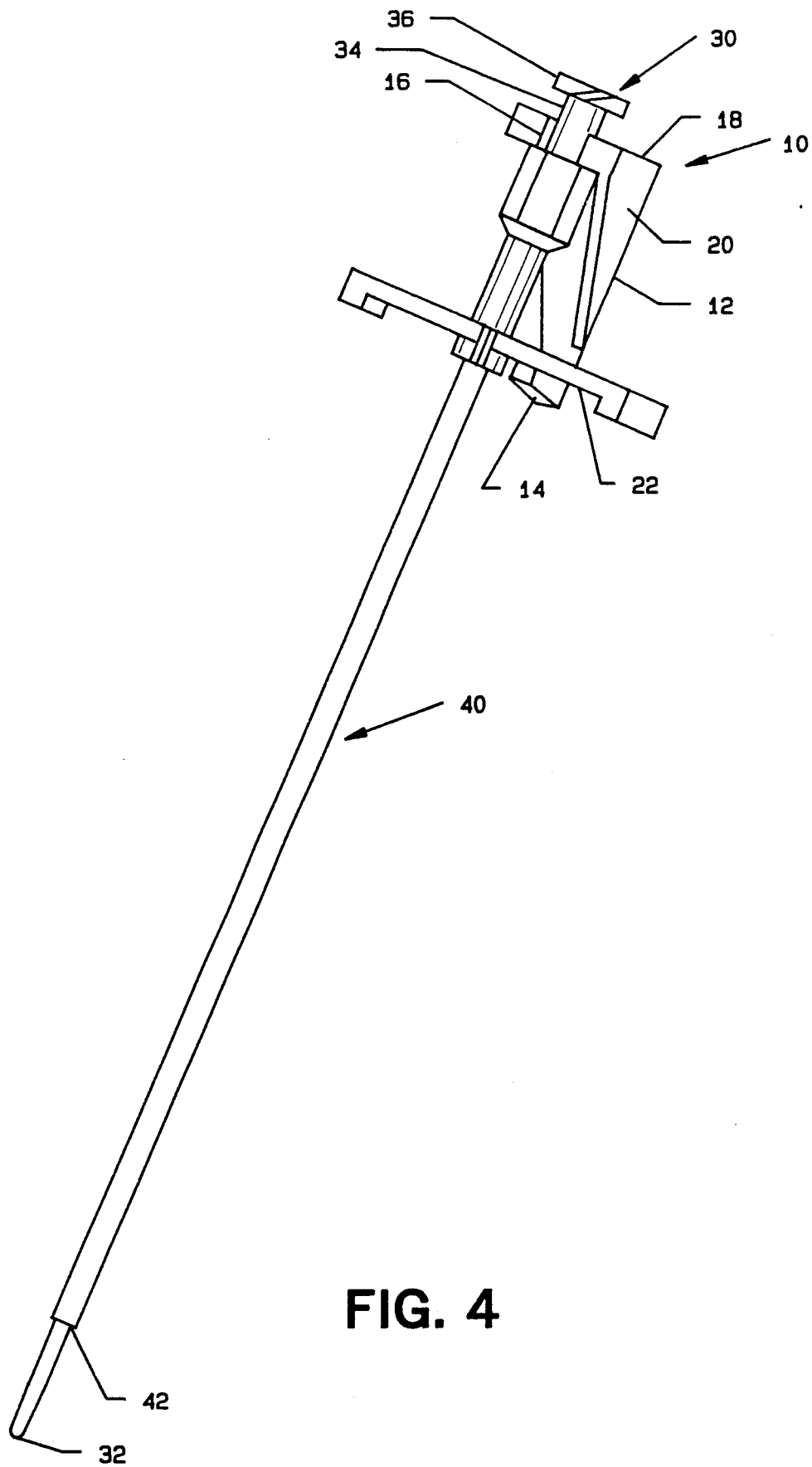
FIG. 4 illustrates a perspective view of the locking clip engaged between a dilator and a sheath; and, FIG. 5 illustrates an alternative embodiment of a locking clip for engagement between a dilator and a sheath.

FIG. 4 illustrates a plan view of the locking clip 10 releasably securing a dilator 30 to a sheath 40. The dilator 30 includes a distal tip 32 extending beyond the distal end 42 of the sheath 40, and a round hub 34 secured to the proximal end 36 of the dilator 30. The locking tooth 14 engages under at least one of the tabs 44 or 46 of the sheath 40, and the snap ring 16 engages about the round hub 34 of the dilator 30, releasably engaging and securing the dilator 30 and the sheath 40 together. The locking tooth surface 22 engages the underside of the tab.

DESCRIPTION OF THE ALTERNATIVE EMBODIMENTS

Figure 5:
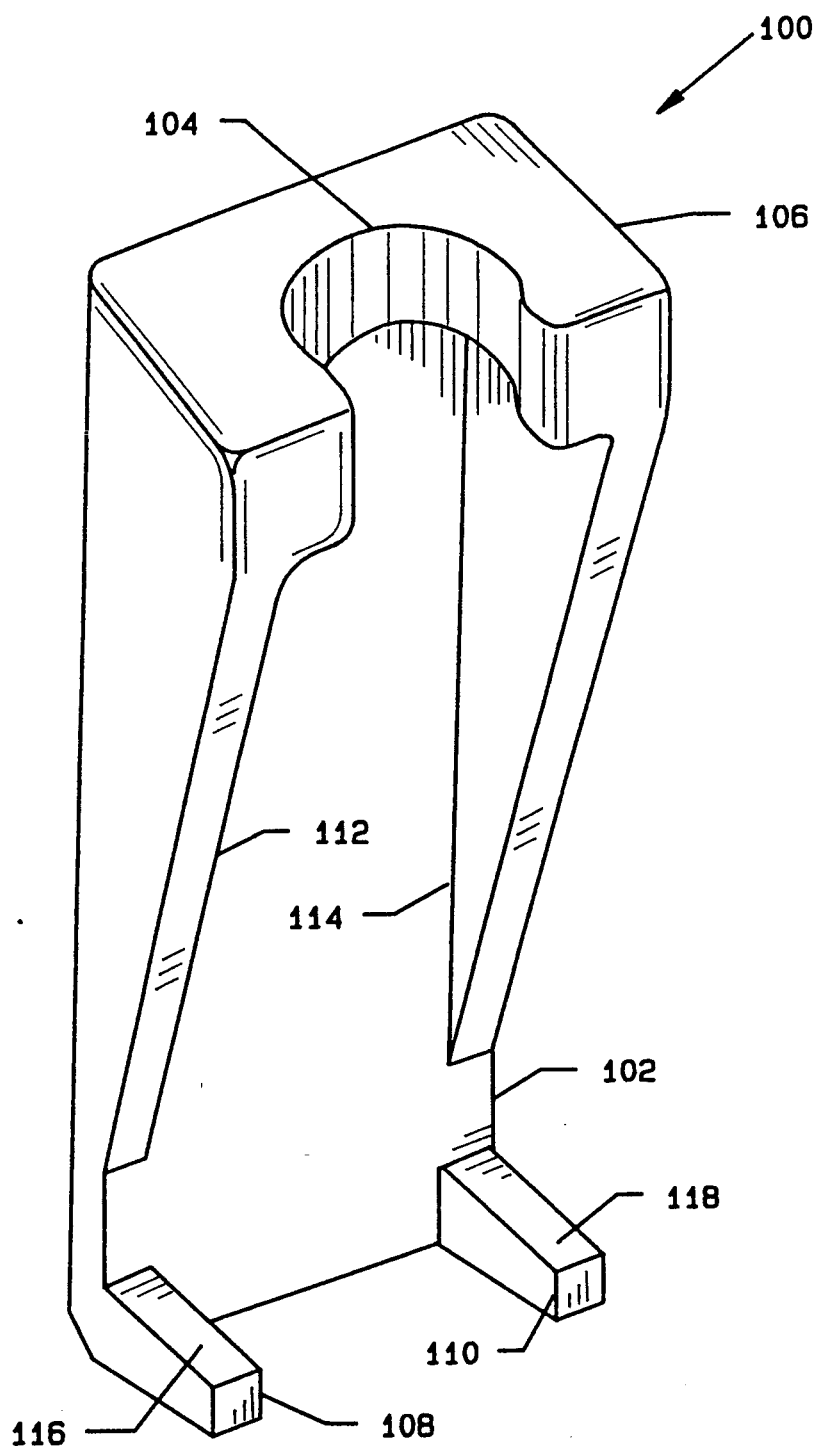

FIG. 5 illustrates an alternative embodiment of a locking clip 100 including a back support 102, a snap ring 104 in a snap ring support member 106, and locking teeth 108 and 110. Optional side supports 112 and 114 can also be provided between the snap ring support member 106 and the back support 102. The locking teeth 108 and 110 include locking teeth engaging surfaces 116 and 118.

Various modifications can be made to the present invention without departing form the apparent scope hereof.

I claim:

1. In combination, a dilator with a hub, a sheath with tabs and a locking clip comprising:
   a. a tear-away sheath with tabs at a proximal end;
   b. a dilator with a distal tip at a distal end and a hub at a proximal end inserted into said tear-away sheath; and
   c. a locking clip including a back support, a snap ring on a snap ring support member at one end and a single only locking tooth at the other end, the snap ring engaged about said hub of said dilator and said locking tooth engaging a one of said tabs of said sheath whereby said locking clip releasably secures said hub of said dilator and said tab of said sheath to form an integral dilator-sheath-locking clip unit during an insertion procedure and said locking clip is releasably snapped away from said hub of said dilator and said tab of said sheath, thereby permitting withdrawal of said dilator after said insertion procedure.

* * * * *